(12) United States Patent
Van Dalen

(10) Patent No.: US 8,337,517 B2
(45) Date of Patent: Dec. 25, 2012

(54) SURGICAL APPARATUS

(75) Inventor: Johan T. W. Van Dalen, Tucson, AZ (US)

(73) Assignee: Eye Care and Cure Pte. Ltd, Singapore (SG)

( * ) Notice: Subject to any disclaimer, the term of this patent is extended or adjusted under 35 U.S.C. 154(b) by 914 days.

(21) Appl. No.: 12/338,796

(22) Filed: Dec. 18, 2008

(65) Prior Publication Data

US 2009/0157093 A1 Jun. 18, 2009

Related U.S. Application Data

(60) Provisional application No. 61/014,667, filed on Dec. 18, 2007.

(51) Int. Cl.
*A61B 17/32* (2006.01)

(52) U.S. Cl. .................................................... 606/167
(58) Field of Classification Search ............... 606/167, 606/1, 130; 600/429; 700/245, 258, 256; 901/36, 41; 907/26, 41
See application file for complete search history.

(56) References Cited

U.S. PATENT DOCUMENTS 6,827,712 B2 * 12/2004 Tovey et al. ........................ 606/1
2008/0097475 A1 * 4/2008 Jaggi et al. .................... 606/130

* cited by examiner

*Primary Examiner* — Elizabeth Houston
*Assistant Examiner* — Katherine M Shi
(74) *Attorney, Agent, or Firm* — Dale F. Regelman; Quarles & Brady LLP

(57) ABSTRACT

A surgical apparatus including a system controller, a hand-held scalpel assembly, a first communication link interconnecting the hand-held scalpel assembly with the system controller, an actuator, and a second communication link interconnecting the actuator with said system controller.

9 Claims, 8 Drawing Sheets

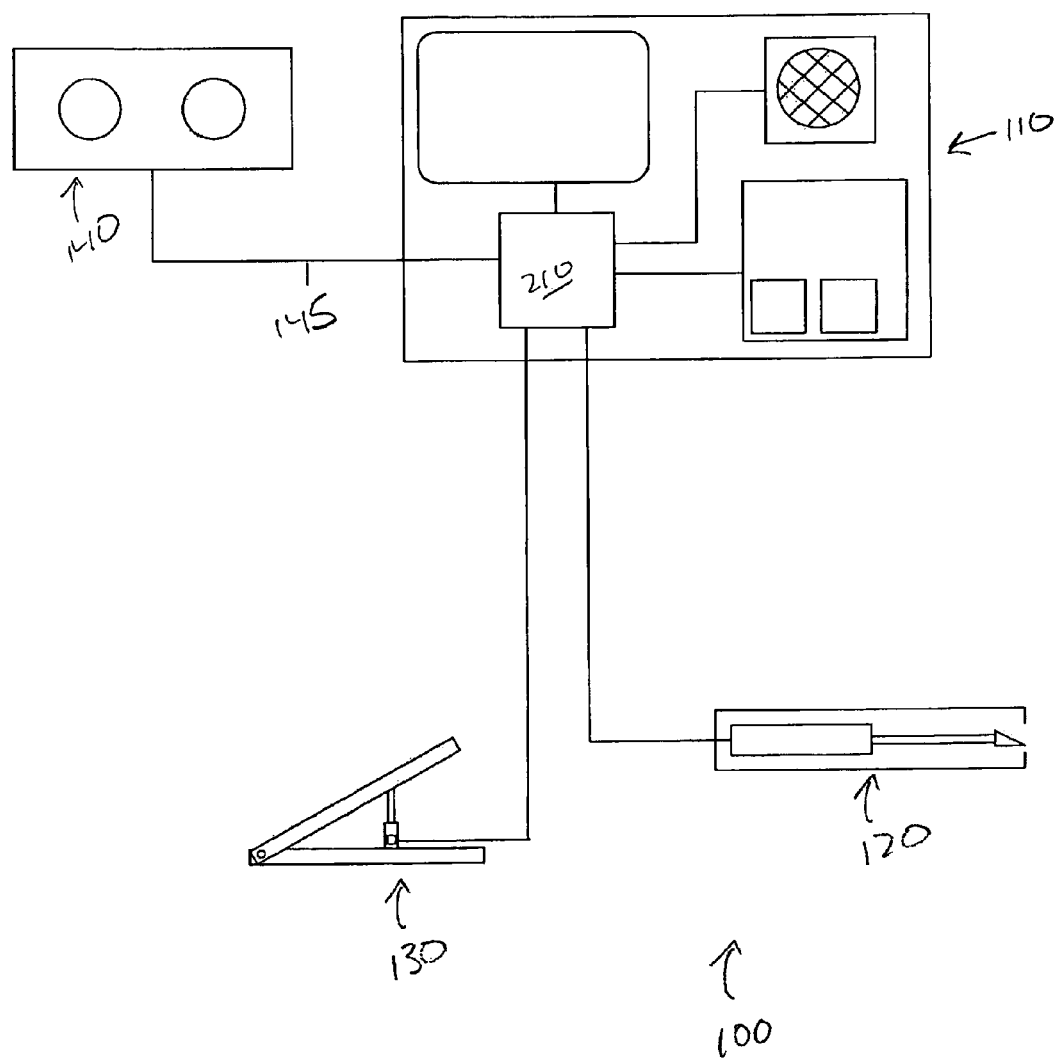

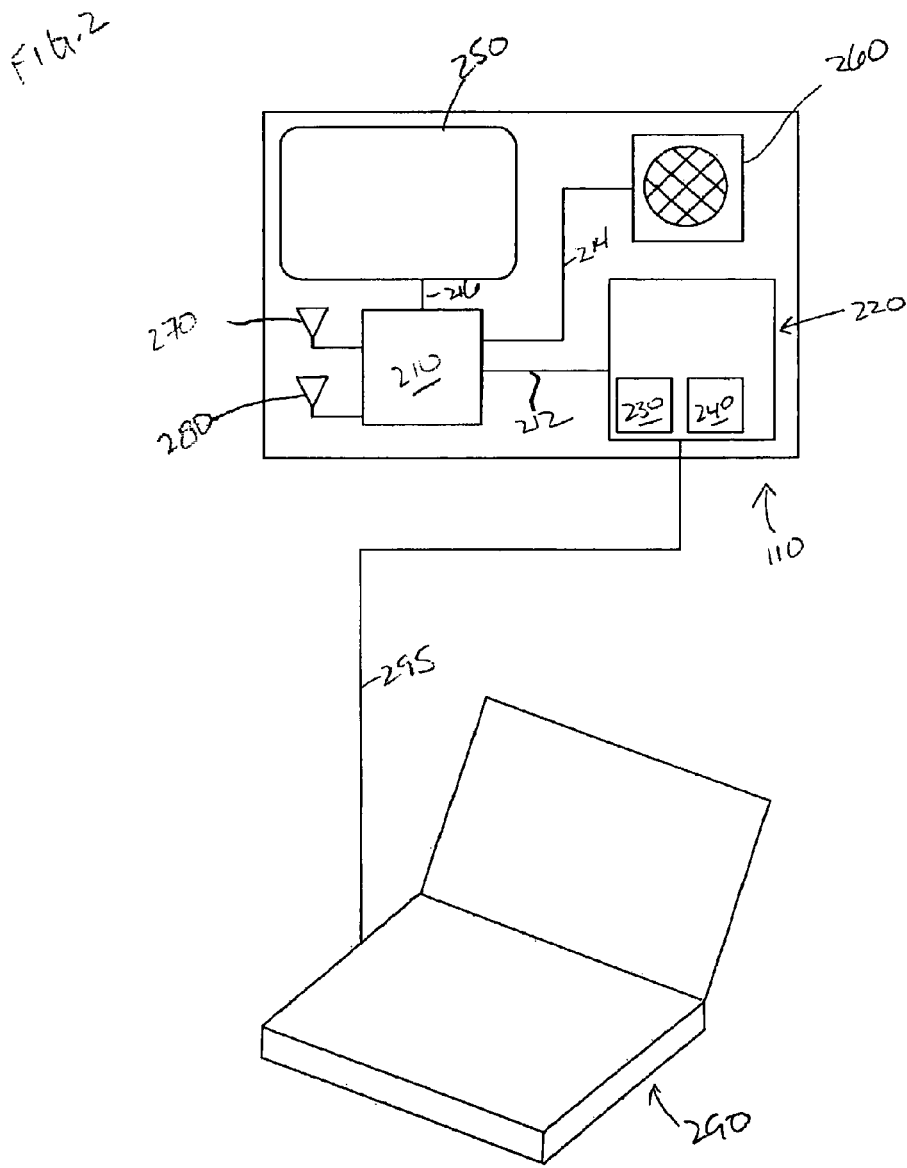

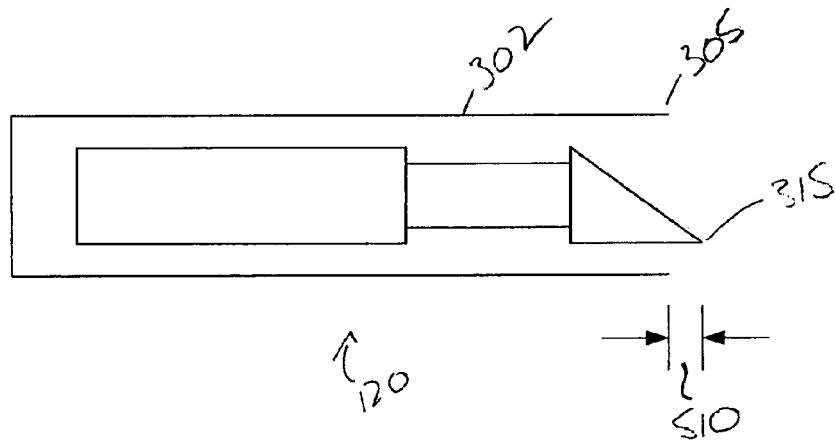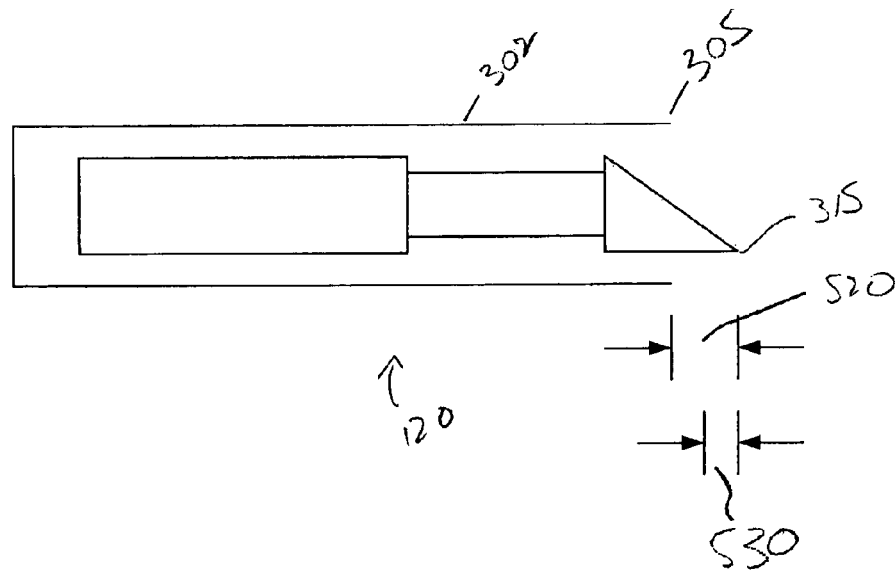

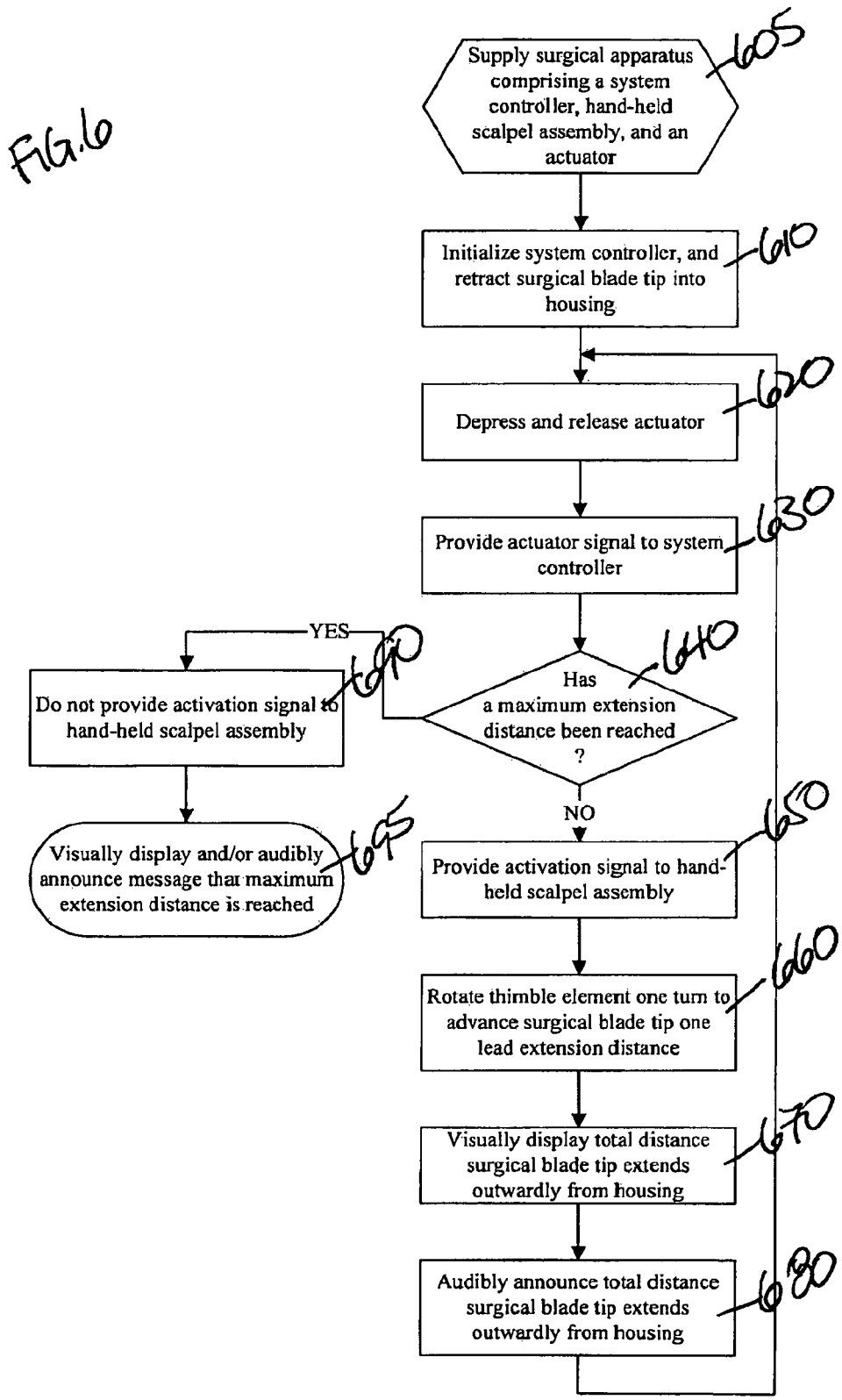

SURGICAL APPARATUS

CROSS-REFERENCE TO RELATED APPLICATIONS

This Application claims priority from a U.S. Provisional Application having Ser. No. 61/014,667, filed Dec. 18, 2007.

BACKGROUND OF THE INVENTION

Ophthalmic surgeons perform surgery on various structures of the eye using a microscope to visualize a surgery field. When forming an incision into an eye tissues, the surgeon must advance a surgical blade tip an initial distance into a tissue structure. The surgeon bases that initial distance upon the known anatomy of the eye.

Often, however, the locations of various tissue structures for an individual patient vary from known and expected nominal anatomical positions. This being the case, achieving an accurate initial surgical blade tip insertion distance can be critical to a successful operation.

SUMMARY OF THE INVENTION

A surgical apparatus is presented, wherein the surgical apparatus comprises a system controller, a hand-held scalpel assembly, a first communication link interconnecting the hand-held scalpel assembly with the system controller, an actuator, and a second communication link interconnecting the actuator with said system controller.

A method using Applicant's surgical apparatus is also presented. When the actuator is moved from a first configuration to a second configuration, an actuator signal to provided to the system controller. Upon receiving an actuator signal, the system controller provides an activation signal to the hand-held scalpel assembly. Upon receiving an activation signal, the hand-held scalpel assembly extends a surgical blade tip a pre-determined distance outwardly from a housing.

BRIEF DESCRIPTION OF THE DRAWINGS

The invention will be better understood from a reading of the following detailed description taken in conjunction with the drawings in which like reference designators are used to designate like elements, and in which:

FIG. 1B is a block diagram illustrating a second embodiment of Applicant's surgical apparatus;

FIG. 2 is a block diagram illustrating a third embodiment of Applicant's surgical apparatus;

FIG. 5A is a block diagram showing Applicant's hand-held scalpel assembly with a surgical blade tip extended a first distance from a housing;

FIG. 5B is a block diagram showing Applicant's hand-held scalpel assembly with a surgical blade tip extended a second distance from a housing;

FIG. 6 is a flow chart summarizing the steps of Applicant's method using Applicant's surgical apparatus.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1A:
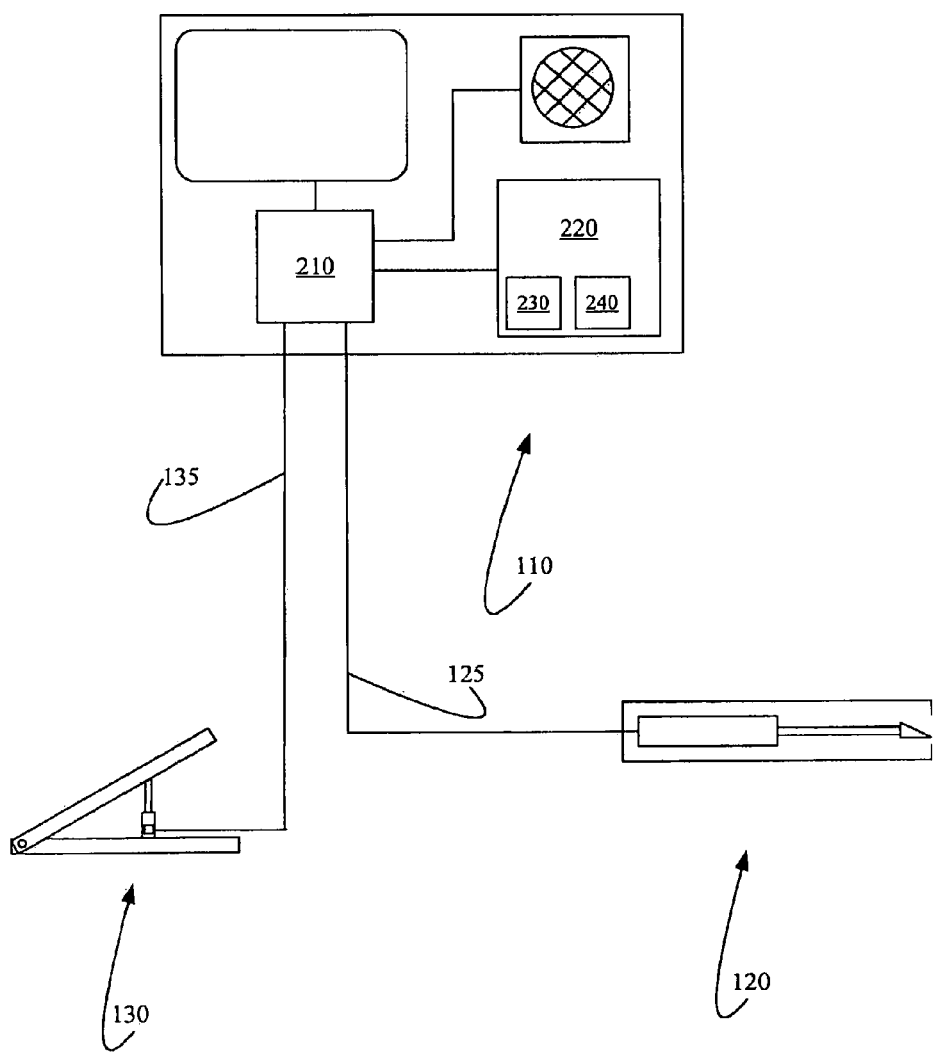
FIG. 1A is a block diagram illustrating one embodiment of Applicant's surgical apparatus.

In the illustrated embodiment of FIG. 1A, Applicant's surgical apparatus 100 comprises system controller 110, hand-held scalpel assembly 120, and actuator 130. System controller comprises processor 210 and computer readable medium 220. In the illustrated embodiment of FIG. 2, microcode/instructions 230 and log 240 are encoded in computer readable medium 220. In certain embodiments, microcode/instructions 230 comprises an operating system, such as and without limitation Windows, AIX, Unix, MVS, LINUX, etc. (Windows is a registered trademark of Microsoft Corporation; AIX is a registered trademark and MVS is a trademark of IBM Corporation; UNIX is a registered trademark in the United States and other countries licensed exclusively through The Open Group; and LINUX is a registered trademark of Linus Torvald). Processor 210 utilizes microcode/instructions 230 to operate Applicant's surgical apparatus.

Hand-held scalpel assembly 120 is interconnected with processor 210 via communication link 125. Actuator 130 is interconnected with processor 210 via communication link 135.

In the illustrated embodiment of FIG. 1B, Applicant's surgical apparatus 100 is shown interconnected to operating microscope 140. As those skilled in the art will appreciate, an ophthalmologist views a surgical field using a microscope while performing surgery. In the illustrated embodiment of FIG. 1B, Applicant's surgical apparatus 100 can interface with an operating microscope via communication link 145 which interconnects the operating microscope and processor 210.

In the illustrated embodiment of FIG. 2, computer readable medium 220 is interconnected with processor 210 via communication link 212, visual display device 250 is interconnected with processor 210 via communication link 216, and audio device 260 is interconnected with processor 210 via communication link 214.

In certain embodiments, computer readable medium 220 comprises non-volatile memory, such as and without limitation battery backed-up RAM, a hard disk drive assembly, an optical disk drive assembly, an electronic memory device, and the like. By "electronic memory device," Applicant means a PROM, EPROM, EEPROM, Flash PROM, compactflash, smartmedia, and the like.

In the illustrated embodiment of FIG. 2, system controller 110 is shown interconnected with computing device 290 via communication link 295. In certain embodiments, computing device 290 comprises a mainframe computer, personal computer, workstation, and combinations thereof. In certain embodiments, system controller 110 comprises hardware, firmware, and software disposed entirely within computing device 290. Communication links 125, 135, 212, 214, 216, and 295, may comprise any I/O interface known, including for example and without limitation, a serial interconnection, such as RS-232 or RS-422, an ethernet interconnection, a SCSI interconnection, an iSCSI interconnection, a Gigabit Ethernet interconnection, a Bluetooth interconnection, a Fibre Channel interconnection, an ESCON interconnection, a FICON interconnection, a Local Area Network (LAN), a private Wide Area Network (WAN), a public wide area network, Storage Area Network (SAN), Transmission Control Protocol/Internet Protocol (TCP/IP), the Internet, and combinations thereof.

In certain embodiments, one or more of communication links 125, 135, and/or 295, comprises a wireless communication link. In certain embodiments, such wireless communication links utilize signals in the infrared spectrum. To facilitate wireless communication with one or more of handheld scalpel assembly 120, actuator 130, and/or computing device 290, in certain embodiments system controller 110 further comprises antenna 270. In certain embodiments, system controller 110 comprises first antenna 270 and second antenna 280.

In certain embodiments, one or more of communication 125, 135, and/or 295, are compliant with one or more of the embodiments of IEEE Specification 802.11 (collectively the "IEEE Specification"). As those skilled in the art will appreciate, the IEEE Specification comprises a family of specifications developed by the IEEE for wireless LAN technology.

The IEEE Specification specifies an over-the-air interface between a wireless client, such as for example projector 100, and a base station or between two wireless clients. The IEEE accepted the IEEE Specification in 1997. There are several specifications in the 802.11 family, including (i) specification 802.11 which applies to wireless LANs and provides 1 or 2 Mbps transmission in the 2.4 GHz band using either frequency hopping spread spectrum (FHSS) or direct sequence spread spectrum (DSSS); (ii) specification 802.11a which comprises an extension to 802.11 that applies to wireless LANs and provides up to 54 Mbps in the 5 GHz band using an orthogonal frequency division multiplexing encoding scheme rather than FHSS or DSSS; (iii) specification 802.11b, sometimes referred to as 802.11 High Rate or Wi-Fi, which comprises an extension to 802.11 that applies to wireless LANS and provides up to about 11 Mbps transmission in the 2.4 GHz band; and/or (iv) specification 802.11 g which applies to wireless LANs and provides 20+Mbps in the 2.4 GHz band.

Figure 3A:
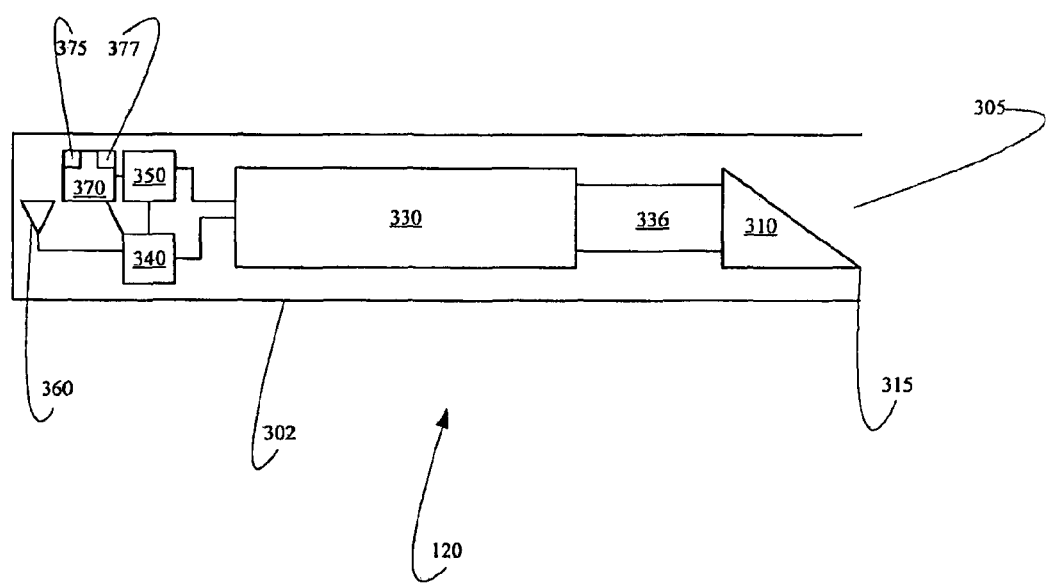
FIG. 3A is a block diagram illustrating Applicant's hand-held scalpel assembly.

Referring now to FIG. 3A, Applicant's scalpel assembly 120 comprises housing 302 formed to include an open end 305. Applicant's scalpel assembly 120 can be sterilized using various sterilization procedures known in the art, such as and without limitation, chemical sterilization, steam sterilization, and/or heat sterilization.

Figure 3B:
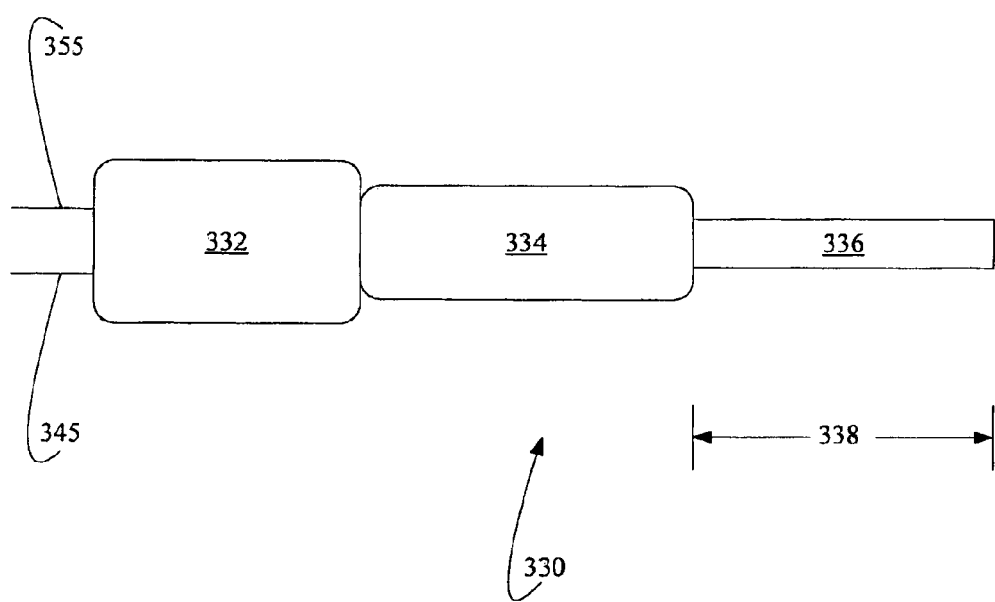
FIG. 3B is a block diagram illustrating Applicant's motorized micrometer element disposed in Applicant's hand-held scalpel assembly.

Scalpel assembly 200 further comprises a surgical blade 310 which can be retracted into housing 302, and moved incrementally outwardly from housing 302 through open end 305. In the illustrated embodiment of FIG. 3A, hand-held scalpel assembly 120 further comprises motorized micrometer 330. Referring to FIG. 3B, motorized micrometer 330 comprises rotatable thimble 332, barrel 334, and spindle 336. Rotating thimble 332 in a first direction causes spindle 336 to extend outwardly from barrel 334. Rotating thimble 332 a full turn, i.e. 360 degrees, in the first direction causes spindle 336 to incrementally extend an extension lead distance outwardly from barrel 334. In certain embodiments, Applicant's extension lead distance is between 0.5 mm and 2.5 mm.

Rotating thimble 332 in a second and opposing direction causes spindle to retract inwardly into barrel 334. Rotating thimble 332 a full turn, i.e. 360 degrees, in the second direction causes spindle 336 to incrementally retract a retraction lead distance inwardly into barrel 334. In certain embodiments, the extension lead distance equals the retraction lead distance. In other embodiments, the extension lead distance differs from the retraction lead distance.

Referring to FIGS. 3A and 3B, surgical blade 310 is removeably attached to a distal end of spindle 336. In certain embodiments, surgical blade 310 is formed from diamond. In certain embodiments, surgical blade 310 comprises stainless steel. In the illustrated embodiment of FIG. 3A, surgical blade 310 comprises surgical blade tip 315.

In the illustrated embodiment of FIG. 3A, scalpel assembly 120 further comprises scalpel processor 340, power source 350, computer readable medium 370, and antenna 360. Further in the illustrated embodiment of FIG. 3A, hand-held scalpel assembly 120 comprises microcode/instructions 375, and retracted position 377, encoded in computer readable medium 370. In certain embodiments, processor 340 comprises an application specific integration circuit ("ASIC"), wherein that ASIC comprises instructions 375 and retracted position 377 encoded therein.

In certain embodiments, microcode 375 comprises computer readable program code comprising a series of computer readable program steps to receive by scalpel processor 340 a retraction signal, wherein in response to that retraction signal scalpel processor 340 causes rotatable thimble to rotate in the second direction to dispose surgical blade 310 in a retracted position such that surgical blade tip 315 is disposed within housing 302. FIG. 3A illustrates surgical blade tip 315 disposed in a retracted configuration.

In certain embodiments, microcode/instructions 375 comprises computer readable program code comprising a series of computer readable program steps to receive by scalpel processor 340 an activation signal, wherein in response to said activation signal scalpel processor 340 causes rotatable thimble to rotate in the first direction 360 degrees to advance surgical blade tip outwardly from open end 305 an incremental extension lead distance.

For example in the illustrated embodiment of FIG. 5A, surgical blade tip 315 is disposed a distance 510 outwardly from open end 305 of housing 305. Referring to FIGS. 5A and 5B, if scalpel processor 340 receives an activation signal, scalpel processor 340 causes rotatable thimble to rotate in the first direction 360 degrees to advance surgical blade tip outwardly an incremental extension lead distance 530, such that surgical blade tip is disposed a total distance 520 from open end 305.

Figure 4A:
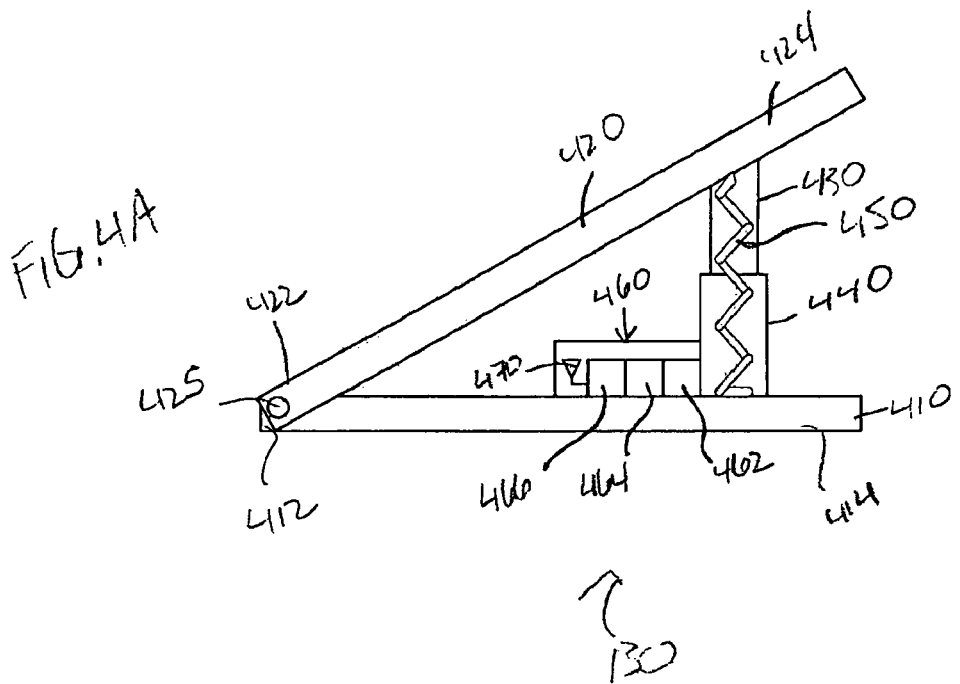
FIG. 4A is a side view of one embodiment of Applicant's actuator, wherein that actuator is disposed in a first configuration.
Figure 4B:
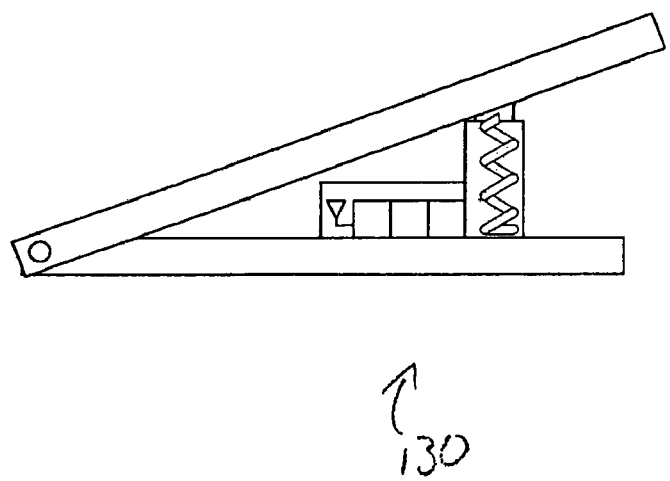
FIG. 4B is a side view of one embodiment of Applicant's actuator, wherein that actuator is disposed in a second configuration.

FIG. 4A illustrates Applicant's actuator 130 comprising a first configuration, i.e. an extended configuration. FIG. 4B illustrates actuator 130 in a second configuration, i.e. a compressed configuration. In the illustrated embodiments of FIGS. 4A and 4B, actuator 130 comprises base 410 and moveable member 420, wherein moveable member 420 is pivotably attached at end 422 to end 412 of base 410. In the illustrated embodiment of FIGS. 4A and 4B, cylindrical member 425 extends through end 422 and end 412 such that member 420 is pivotably attached to base 410.

In the illustrated embodiments of FIGS. 4A and 4B, actuator 130 further comprises tubular member 430 which is partially slidably disposed within tubular member 440, wherein one end of tubular member 440 is attached to end 414 of base 410 and extends upwardly therefrom, and wherein one end of tubular member 430 is attached to end 424 of member 420 and extends downwardly therefrom. In the illustrated embodiment of FIGS. 4A and 4B, spring 450 is disposed within tubular members 440 and 450 such that one end of spring 450 is attached to base 410 and the opposing end of spring 450 is attached to member 420.

If a downward force is exerted on member 420, member 420 can be pivoted around interconnecting member 425 to place actuator 130 in the second configuration of FIG. 4B. When that downward force is released, spring 450 urges member 420 upwardly such that actuator 130 returns to the first configuration of FIG. 4A.

In certain embodiments, actuator 130 is disposed on a floor, wherein pivotable member 420 is urged downwardly using foot pressure. In other embodiments, actuator 130 comprises a hand-held device, wherein pivotable member 420 is urged downwardly using hand pressure.

In certain embodiments, actuator 130 comprises an actuator controller 460, wherein that actuator controller 460 comprises a computer readable medium 462, microcode/instructions 464 encoded in computer readable medium, actuator processor 466, and optionally antenna 470. When actuator 130 is placed in the second configuration of FIG. 4B, processor 466 provides an actuator signal to processor 210. In certain embodiments, when actuator 130 is placed in the second configuration of FIG. 4B, processor 466 wirelessly provides an actuator signal to processor 210. In certain embodiments, microcode/instructions 464 comprises computer readable program code comprising a series of computer readable program steps to provide by actuator processor 466 an actuator signal to system processor 210 when actuator 130 is placed in the second configuration of FIG. 4B. In response to receiving an actuator signal, system controller 110 provides an activation signal to scalpel assembly 120, wherein each such activation signal causes surgical blade 310 to move an extension lead distance increment outwardly from housing 305.

Applicant's invention comprises a method to control the distance surgical blade tip 315 (FIG. 3A) extends outwardly from housing 302 (FIG. 3) using actuator 130 (FIGS. 1, 4A, 4B). Referring now to FIG. 6, in block 605 the method provides a surgical apparatus, such as surgical apparatus 100, comprising a system controller, an actuator, and a hand-held scalpel assembly.

In block 610, the method initializes the system controller. In certain embodiments, when system controller is powered on, system processor 210 provides a retraction signal to handheld-scalpel assembly thereby causing surgical blade tip 315 to be retracted within housing 302. In certain embodiments, a retracted position 377 is encoded in computer readable medium 370 disposed within hand-held scalpel assembly 120. FIG. 3A shows surgical blade tip 315 is a retracted configuration.

In block 620, the actuator of block 605 is moved from a first configuration of FIG. 4A to a second configuration of FIG. 4B. In block 630, the method provides an actuator signal to the system controller of block 605. In certain embodiments in block 630 an actuator processor 466 provides an actuator signal to a system processor 210 disposed in the system controller 110.

In block 640, the method determines if a pre-determined maximum extension of surgical blade tip 315 from open end 305 of housing 302 has been reached. In certain embodiments, block 640 is performed by a system controller. In certain embodiments, block 640 is performed by a hand-held scalpel processor.

If the method determines that a pre-determined maximum extension of surgical blade tip 315 from open end 305 of housing 302 has been reached, the method transitions from block 640 to block 690 wherein the method does not provide an actuation signal to the hand-held scalpel assembly of block 605. In certain embodiments, the system controller of block 605 comprises a visual display device. In these embodiments, in block 695 the method visually displays a message that a maximum surgical blade tip extension distance has been reached. In certain embodiments, the system controller of block 605 comprises an audio device, such as for example and without limitation audio device 260 (FIG. 2). In these embodiments, in block 695 the method audibly announces a message that a maximum surgical blade tip extension distance has been reached.

If the method determines in block 640 that a maximum surgical blade extension distance has not been reached, the method transitions from block 640 to block 650 wherein the method provides an activation signal to the hand-held scalpel assembly of block 605. In certain embodiments, a system controller performs block 640. In certain embodiments, a system processor disposed in a system controller performs block 640.

In block 660, the method extends a surgical blade tip outwardly a pre-determined distance from the hand-held scalpel assembly of block 605. In certain embodiments, in block 660 the method rotates a thimble 332 of a motorized micrometer 330 disposed within the hand-held surgical assembly 120 thereby extending a moving spindle 336 an extension lead distance outwardly from barrel 334, thereby extending surgical blade tip 315 an incremental extension lead distance outwardly through open end 305 of housing 302.

In block 670, the method visually displays in fractions of inches or millimeters a total distance that surgical blade tip 315 has been advanced outwardly from the hand-held scalpel assembly of block 605. In certain embodiments in block 670, the total distance that surgical blade tip 315 has been advanced outwardly through open end 305 is visually displayed on visual display device 250. For example, if surgical blade tip 315 is presented disposed a distance 510(FIG. 5A) outwardly from open end 305 of housing 305, and if surgical blade tip is subsequently advanced to a distance 520 (FIG. 5B) outwardly from open end 305, then in block 670 the visual display is updated to display in fractions of inches or millimeters that new distance 520.

In block 680, the method announces using audio device 260 a total distance in fractions of inches or millimeters that surgical blade tip 315 has been advanced outwardly from end 305. For example, if surgical blade tip is advanced from distance 510 to distance 520, then in block 680 that new distance 520 in fractions of inches or millimeters is announced from audio device 260.

Applicant's method transitions from block 680 to block 620 and continues as described herein.

In certain embodiments, each distance that surgical blade tip has been advanced outwardly from end 305, and the time of each such advancement, are recorded in log 240 encoded in computer readable medium 220. In certain embodiments, system processor 210 performs such logging functions.

In certain embodiments of Applicant's method, each time actuator 130 is moved to the second configuration of FIG. 4B, actuator controller 460 provides a single actuator signal to system controller 110. In these embodiments, surgical blade tip 315 is moved outwardly from housing 305 a single increment 530 each time actuator 130 is placed in the second configuration of FIG. 4B. In order to move surgical blade tip further outwardly, actuator 130 must be returned to the first configuration of FIG. 4A, and then again moved to the second configuration of FIG. 4B.

In other embodiments of Applicant's method, as along as actuator 130 remains in the second configuration of FIG. 4B, actuator controller 460 continues to provide actuator signals to system controller 110, and system controller 110 continues to provide activation signals to hand-held scalpel assembly 120, and surgical blade tip 315 continues to move outwardly from end 505 of housing 305.

In certain embodiments of Applicant's method, an extension lead distance can be set and stored in computer readable medium 220. In certain embodiments of Applicant's method, a maximum extension distance can be set and stored in computer readable medium 220. In these embodiments, if that maximum extension distance is reached, Applicant's system controller 110 will not provide additional activation signals to the hand-held scalpel assembly 120. In certain of these embodiments, if that maximum extension distance is reached, Applicant's system controller 110 will display a message on visual display device 250. In certain of these embodiments, if that maximum extension distance is reached, Applicant's system controller 110 will cause an audible message to be announced from audio device 260.

In certain embodiments, Applicant's invention includes instructions encoded in microcode/instructions 230 (FIG. 1A), and/or microcode/instructions 375 (FIG. 3A), and/or microcode/instructions 464 (FIG. 4A), residing in computer readable medium, such as for example computer readable medium 220 (FIG. 1), computer readable medium 370, and/or computer readable medium 462, respectively, wherein those instructions are executed by a processor, such as processor 210 (FIG. 1), processor 340, and/or processor 466, respectively, to perform one or more of blocks 610, 620, 630, 640, 650, 660, 670, 680, 690, and/or 695, recited in FIG. 6.

While the preferred embodiments of the present invention have been illustrated in detail, it should be apparent that modifications and adaptations to those embodiments may occur to one skilled in the art without departing from the scope of the present invention.

I claim:

1. A surgical apparatus, comprising:
a system controller;
a hand-held scalpel assembly;
a first communication link interconnecting said hand-held scalpel assembly with said system controller;
an actuator;
a second communication link interconnecting said actuator with said system controller;
wherein said system controller comprises:
  a system processor;
  a first computer readable medium in communication with said system processor;
  system microcode encoded in said first computer readable medium;
  a visual display device in communication with said system processor;

wherein said hand-held scalpel assembly comprises:
  a scalpel processor;
  a power source interconnected to said scalpel processor;
  a second computer readable medium interconnected to said power source;
  scalpel microcode encoded in said second computer readable medium;
  a motorized micrometer interconnected to said scalpel processor and interconnected to said power source, wherein said motorized micrometer comprises a rotatable thimble, a barrel having a first end attached to said rotatable thimble, and a spindle comprising a distal end extending outwardly from a second end of said barrel;
  a surgical blade attached to said distal end, wherein said surgical blade comprises a surgical blade tip;
  a housing formed to include an open end, wherein said scalpel processor, said power source, said computer readable medium, and said motorized micrometer, are disposed within said housing; and
  wherein said scalpel processor can cause said thimble to rotate in a first direction, thereby causing said spindle to move inwardly into said barrel, thereby causing said surgical blade tip to retract within said housing through said open end; and
  wherein said scalpel processor can cause said thimble to rotate in a second direction, thereby causing said spindle to move outwardly from said barrel, thereby causing said surgical blade tip to extend outwardly from said housing through said open end;
wherein said motorized micrometer comprises:
  a extension lead distance comprising a distance said spindle moves inwardly upon a 360 degree rotation of said thimble in said first direction;
  a retraction lead distance comprising a distance said spindle moves outwardly upon a 360 degree rotation of said thimble in said second direction;
wherein:
  said actuator is disposed in a first configuration;
  said actuator can be moved from a first configuration to a second configuration;
  said actuator provides an actuator signal to said system processor if said actuator is moved from said first configuration to said second configuration;
  said actuator comprises, a base, a pivotable member having a first end pivotally attached to said base;
  when said actuator is disposed in said first configuration said pivotable member extends slopingly upwardly from said base;
  when said actuator is disposed in a second configuration said pivotable member is parallel to said base;
wherein said actuator further comprises:
  an actuator controller comprising an actuator processor, a third computer readable medium, and actuator microcode encoded in said third computer readable medium;
  a restoring means to move said second end of said pivotable member upwardly from said second configuration to said first configuration
  wherein said actuator controller provides said actuator signal to said system controller when said pivotable member is moved from said first configuration to said second configuration.

2. The surgical apparatus of claim 1, wherein said actuator microcode comprises computer readable program code comprising a series of computer readable program steps to effect providing said actuator signal to said system controller when said pivotable member is moved from said first configuration to said second configuration.

3. The surgical apparatus of claim 1, wherein:
when said system controller receives an actuator signal, said system controller provides an activation signal to said scalpel processor;
when said scalpel processor receives an activation signal, said scalpel processor causes said rotatable thimble make a single 360 degree rotation.

4. The surgical apparatus of claim 3, wherein said system microcode comprises computer readable program code comprising a series of computer readable program steps to effect providing an activation signal to said scalpel processor when said system controller receives an actuator signal.

5. The surgical apparatus of claim 4, wherein said scalpel microcode comprises computer readable program code comprising a series of computer readable program steps to effect rotating said thimble a single 360 degree rotation when said scalpel processor receives an activation signal.

6. The surgical apparatus of claim 4, wherein when said scalpel processor receives an activation signal, said scalpel processor causes said rotatable thimble to make a single 360 degree rotation thereby moving said surgical blade tip outwardly from an existing distance from said open end to a new distance from said open end, wherein said new distance from said open end equals said existing distance from said open end plus said extension lead distance.

7. The surgical apparatus of claim 6, wherein said controller further comprises a speaker in communication with said system processor, said method further comprising audibly announcing said new distance using said audio device.

8. The surgical apparatus of claim 7, wherein said system microcode comprises computer readable program code comprising a series of computer readable program steps to effect audibly announcing said new distance using said audio device.

9. The surgical apparatus of claim 4, wherein said system microcode comprises computer readable program code comprising a series of computer readable program steps to effect moving said surgical blade tip to a retracted configuration when said system controller is powered on.

\* \* \* \* \*